(12) United States Patent
Damaceno et al.

(10) Patent No.: US 10,405,546 B2
(45) Date of Patent: Sep. 10, 2019

(54) AGROCHEMICAL SUSPOEMULSIONS

(75) Inventors: Antonio Carlos Damaceno, Hongkong (CN); Jose Gilberto Hermann, Hongkong (CN)

(73) Assignee: ROTAM AGROCHEM INTERNATIONAL COMPANY LIMITED, Chai Wan (HK)

( * ) Notice: Subject to any disclaimer, the term of this patent is extended or adjusted under 35 U.S.C. 154(b) by 275 days.

(21) Appl. No.: 13/128,263

(22) PCT Filed: Jan. 11, 2010

(86) PCT No.: PCT/CN2010/070112
§ 371 (c)(1),
(2), (4) Date: May 9, 2011

(87) PCT Pub. No.: WO2010/078852
PCT Pub. Date: Jul. 15, 2010

(65) Prior Publication Data
US 2011/0257166 A1      Oct. 20, 2011

(30) Foreign Application Priority Data
Jan. 12, 2009   (BR) .................................. PI0900019

(51) Int. Cl.
| A01N 43/653 | (2006.01) |
| A01P 3/00 | (2006.01) |
| A01P 1/00 | (2006.01) |
| A01N 43/88 | (2006.01) |
| A01N 37/50 | (2006.01) |
| A01N 43/54 | (2006.01) |

(52) U.S. Cl.
CPC ............. *A01N 37/50* (2013.01); *A01N 43/54* (2013.01); *A01N 43/653* (2013.01); *A01N 43/88* (2013.01)

(58) Field of Classification Search
CPC ........ A01N 65/00; A01N 25/04; A01N 53/00; A01N 25/34; A61Q 17/005
See application file for complete search history.

(56) References Cited

U.S. PATENT DOCUMENTS

| 2005/0169951 A1* | 8/2005 | Sasson et al. ................ 424/405 |
| 2006/0171979 A1* | 8/2006 | Calvo et al. .................. 424/405 |
| 2007/0053944 A1 | 3/2007 | Vermeer |
| 2010/0234230 A1* | 9/2010 | Fowler .......................... 504/289 |

FOREIGN PATENT DOCUMENTS

| CN | 1960632 | 5/2007 |
| CN | 101322494 A | 12/2008 |
| DE | 4341986 A1 | 6/1995 |
| WO | 2008/145063 A1 | 12/2008 |

OTHER PUBLICATIONS

International Search Report PCT/CN2010/070112; dated Apr. 15, 2010.
"Diamant", Internet Citation, Oct. 16, 2008, pp. 1-13, Retrieved from Internet: URL:http://www.agricentre.basf.co.uk/uk/deploy/media/uk_ie_internet/product_files_uk/labels/Diamant.pdf [retrieved on Dec. 3, 2009].
Extended European Search Report for Application No./Patent No. 10729111.4-2103/2375901, dated Jul. 2, 2012.

* cited by examiner

*Primary Examiner* — Kathrien A Cruz
*Assistant Examiner* — Andrew P Lee
(74) *Attorney, Agent, or Firm* — Dickinson Wright PLLC

(57) ABSTRACT

The present invention provides an aqueous suspoemulsion comprising (a) an oil phase comprising (i) at least one triazole active compound as emulsified component, solid at room temperature, (ii) at least one alkyl carboxylic acid amide as a solvent and a crystal growth inhibitor, and (iii) a polymeric stabilizer, and (b) a continuous water phase comprising (i) at least one strobilurin active compound as suspended solid component, solid at room temperature, (ii) at least one dispersant selected from the group consisting of methacrylic acid-methyl methacrylate-polyethyleneglycol graft copolymer, tristyrylphenolethoxylates and/or propylene oxide/ethylene oxide block copolymer with 10% to 50% EO, preferably with 20% to 50% EO and most preferably with 30% to 40% EO, (iii) water, and (iiii) additives, if appropriate. a process for preparing the suspoemulsion and its use for applying the active compounds comprised therein to plants and/or their habitat are also provided.

20 Claims, No Drawings

AGROCHEMICAL SUSPOEMULSIONS

The present invention relates to novel suspoemulsion formulations for agrochemical active ingredients and their use in the treatment of pests at a locus.

BACKGROUND

Numerous suspension concentrates of agrochemically active compounds are already known. Thus, suspension concentrates of tebuconazole, or azoxystrobin, or a combination of a triazole and a strobilurin, such as a combination of Azoxystrobin plus Cyproconazole or Trifloxistrobin plus Tebuconazole, have been commercial products. It has been found that the suspension concentrate of the combination of a triazole and a strobilurin has a higher activity than the corresponding single compound suspension concentrate when being diluted with water. Mixture of different biolocally active compounds can have a broader spectrum of activity than a single compound alone. Furthermore, these can exhibit a synergistic effect compared with the single active ingredient. However the combination of a strobilurin and a triazole suspension concentrate, such as a combination of Azoxystrobin plus Cyproconazole or Trifloxistrobin plus Tebuconazole, has the disadvantage that the activity is weaker than that of sprays obtainable by diluting a triazole emulsion concentrates, such as tebuconazole emulsion concentrates, with water.

US2007/0053944 A1 discloses certain novel suspension concentrates comprising at least one active compound selected from the group consisting of azoles and/or the strobilurins. It is indicated that biological activities of the sprays obtained by diluting suspension concentrates according to US2007/0053944 with water come close to the activities of the sprays obtainable from the corresponding emulsion concentrates. Formulations according to the invention in US2007/0053944 appear to enhance the biological activities of the active components comprised therein so that, compared to customary suspension preparations, either a higher activity is achieved or less active compound is required. However sprays preparable by diluting the suspension concentrates or other formulations comprising the combination of a triazole and a strobilurin as the active ingredients have not been found which show a considerably better biological activity than sprays obtainable from the corresponding customary emulsion concentrates.

Therefore, it would be advantageous to provide a composition comprising both a triazole and a strobilurin as the active ingredients which demonstrates a considerably better biological activity than the corresponding customary emulsion concentrates comprising a triazole as the active ingredient, such as tebuconazole emulsion concentrates.

It would be very desirable to provide such a product that is friendly to the environment. Emulsion concentrates comprising a triazole as the active ingredient show good efficacy. However this formulation needs more solvents which bring pollution to the environment.

SUMMARY OF THE INVENTION

This present invention now provides a novel aqueous suspoemulsion (SE) product comprising as suspended solid component a strobilurin, and as emulsified component a triazole.

This present invention also provides a suspoemulsion composition which demonstrates a considerably better biological activity than the corresponding customary emulsion concentrates comprising a triazole as the active ingredient, such as tebuconazole emulsion concentrates.

Accordingly, in a first aspect, the present invention provides an aqueous suspoemulsion, characterized in that it comprises the components:
(a) a dispersed oil phase comprising:
  (i) a solvent having at least one triazole active compound dissolved therein; and
(b) a continuous water phase comprising:
  (i) water having at least one strobilurin active compound suspended therein.

The oil phase, component (a), may contain one or more solvents and crystal growth inhibitors, preferably at least one alkyl carboxylic acid amide acting as both a solvent and a crystal growth inhibitor. In addition, component (a) may also comprise one or more polymeric stabilizers.

The continuous water phase, component (b), may further comprise one or more dispersants. Particularly preferred dispersants are those selected from the group consisting of methacrylic acid-methyl methacrylate-polyethyleneglycol graft copolymers, tristyrylphenolethoxylates and/or propylene oxide/ethylene oxide block copolymer with 10% to 50% EO, preferably with 20% to 50% EO, and more preferably with 30% to 40% EO. Preferably two such dispersants are present in component (b).

Accordingly, in one preferred embodiment, the composition of the present invention is an aqueous suspoemulsion, characterized in that it comprises:
(a) an oil phase comprising:
  (i) at least one triazole active compound as emulsified component, solid at room temperature;
  (ii) at least one alkyl carboxylic acid amide as a solvent and crystal growth inhibitor; and
  (iii) a polymeric stabilizer; and
(b) a continuous water phase comprising:
  (i) at least one strobilurin active compound as suspended solid component, solid at room temperature;
  (ii) at least one dispersant selected from the group consisting of methacrylic acid-methyl methacrylate-polyethyleneglycol graft copolymers, tristyrylphenolethoxylates and/or propylene oxide/ethylene oxide block copolymer with 10% to 50% EO, preferably with 20% to 50% EO, and more preferably with 30% to 40% EO; and
  (iii) water.

In a further aspect, the present invention provides a process for preparing a suspoemulsion as hereinbefore described, characterized in that it comprises the steps:

Step 1: Preparing the Triazole EC phase by mixing the active triazole ingredient with an alkyl carboxylic acid amide, which acts as a solvent and a crystal growth inhibitor, and a polymeric stabilizer;

Step 2: Preparing a dispersion of particles of the strobilurin active ingredient in a continuous water phase by mixing the active ingredient, a dispersant and a required amount of water; and Step 3: Combining the oil phase produced in Step 1 with the water phase produced in Step 2.

Use of the suspoemulsion described above and a method of treating pests at a locus comprising applying the suspoemulsion are also provided by the present invention.

DETAILED DESCRIPTION OF THE INVENTION

A suspoemulsion (SE) is a combination of an emulsion concentrate (EC) of one component with a suspension concentrate (SC) of the other. An EC phase is one in which the first active ingredient is dissolved in oil. An SC is a suspension of the other active ingredient in water. When the two are mixed, water, as the continuous phase in the emulsion, carries oil droplets, as the dispersed phase containing one active ingredient, is intermingled with suspended particles of the other. Generally the SC, and hence the resulting SE, additionally contains other components such as a dispersant to aid the stability of the suspension and hence of the whole system.

The suspoemulsion of the invention may be produced in a known manner and using techniques known to the one skilled in the art. In particular, the suspoemulsion may be prepared as follows:

Step 1: Preparation of Triazole EC phase: The Active ingredient from Triazole family is mixed with an alkyl carboxylic acid amide, which acts as a solvent and a crystal growth inhibitor, along with suitable emulsifiers and a polymeric stabilizer between the oil droplets and the dispersed solid particles which are described in Step 2.

Step 2: Preparation of Dispersed particles of Active ingredient from Strobilurin family in a continuous water phase:

The Active ingredient from Strobilurin family along with suitable dispersants like tristyrylphenolethoxylates and a polymeric block copolymer with 10% to 50% EO, preferably with 20% to 50% EO and most preferably with 30% to 40% EO, other additives such as anti-freezing agent and anti-foaming agent, and a required amount of water are initially mixed well and finely milled using a horizontal agitating bead mill maintaining the process parameters like the average particle size d50 not to exceed 3 microns and for almost all the particles d90 not to exceed 6 microns.

Step 3: The step 1 oil phase is added to the step 2 water phase under continuous agitation for an optimum amount of time.

Step 4: The thickeners, like polysaccharides or Xanthan gums, are prepared in advance to enable them to be hydrated and be ready for the addition in the following step as mentioned as Step 5.

Step 5: Suitable quantity of the thickener such as a gum is added to the mixture in step 4 and continuously agitated till the mixture is a homogeneous suspension. The suspension is tested for the viscosity and pourability test and subsequently all the other physico-chemical tests.

The suspoemulsion according to the invention comprise two or more solid active compounds selected from the group consisting of triazoles and strobilurins.

In this context, the following fungicidally active compounds may be mentioned as examples of triazoles as emulsified components in the suspoemulsion according to the invention:

azaconazole, bitertanol, bromuconazole, cyproconazole, diclobutrazole, difenoconazole, diniconazole, epoxiconazole, etaconazole, fenbuconazole, fluquinconazole, flusilazole, flutriafol, hexaconazole, imibenconazole, ipconazole, metconazole myclobutanil, paclebutrazol, penconazole, propiconazole, prothioconazole, simeconazole, tebuconazole, tetraconazole, triadimefon, triademenol, triconazole.

Preference is given to:
Tebuconazole, prothioconazole, triadimefon, triadimenol, bitertanol, diclobutrazole, propiconazole, difenoconazole, cyproconazole, flutriafol, hexaconazole, myclobutanil, penconazole, etaconazole, bromuconazole, epoxiconazole, fenbuconazole, tetraconazole, diniconazole, triticonazole, flusilazole, prochloraz, metconazole, ipconazole and fluquinconazole.

The following fungicidally active compounds may be mentioned as examples of strobilurins as suspended solid components in the suspoemulsion according to the invention:

azoxystrobin, dimoxystrobin, famoxadone, fenamidone, fluoxastrobin, kresoxim-methyl, metaminostrobin, picoxystrobin, pyraclostrobin and trifloxystrobin, Preference is given to:
Trifloxystrobin, fluoxastrobin, kresoxim-methyl, azoxystrobin, picoxystrobin, pyraclostrobin and metominostrobin.

The suspoemulsion according to the invention preferably comprises in the oil phase one or more crystal growth inhibitors, which are more preferably selected from the group consisting of alkyl carboxylic acid amides, in order to inhibit crystallization of the emulsified triazole fungicidal component, such as tebuconazole, which have a tendency to crystallize. Here, preference is given to alkyl carboxylic acid amides of the formula (I)

$$R-\overset{O}{\underset{\|}{C}}-N\overset{R^1}{\underset{R^2}{\diagup}}\quad\text{(I)}$$

in which:
R represents $C_3$-$C_{19}$-alkyl,
$R^1$ represents $C_2$-$C_6$-alkyl, and
$R^2$ represents $C_2$-$C_6$-alkyl,
for preventing crystallization of agrochemical active substances when spraying onto plants.

R in the compounds of formula (I) is preferably an unbranched or branched, saturated or unsaturated, especially preferably unbranched, saturated alkyl group having 5 to 11 carbon atoms, very especially preferably n-heptyl or n-nonyl or n-undecyl.

$R^1$ and $R^2$ are preferably identical or different, especially preferably identical, and an unbranched or branched, especially preferably unbranched alkyl group having 2 to 4 carbon atoms.

Preferred compounds of the formula (I) are therefore those of the formula (Ia) in which $R^1$ and $R^2$ are identical having 2 carbon atoms.

$$R-CO-N(C_2H_5)_2 \quad\text{(Ia)}$$

in which:
R has the above-mentioned meanings.

The following are very especially preferred: N,N-diethyl-n-hexanamide, N,N-diethyl-n-octanamide, N,N-diethyl-n-decanamide and N,N-diethyl-n-dodecanamide, in particular N,N-diethyl-n-octanamide, N,N-diethyl-n-decanamide and N,N-diethyl-n-dodecanamide.

Other preferred compounds of the formula (I) are therefore those of the formula (Ib) in which $R^1$ and $R^2$ are identical having 3 carbon atoms.

$$R-CO-N(C_3H_7)_2 \quad\text{(Ib)}$$

in which:
R has the above-mentioned meanings.

The following are very especially preferred: N,N-dipropyl-n-hexanamide, N,N-dipropyl-n-octanamide, N,N-dipropyl-n-decanamide and N,N-dipropyl-n-dodecanamide, in particular N,N-dipropyl-n-octanamide, N,N-dipropyl-n-decanamide and N,N-dipropyl-n-dodecanamide.

Finally, further preferred compounds of the formula (I) are therefore those of the formula (Ic) in which $R^1$ and $R^2$ are identical having 4 carbon atoms.

R—CO—N(C$_4$H$_9$)$_2$ (Ic)

in which:
R has the above-mentioned meanings.

The following are very especially preferred: N,N-dibutyl-n-hexanamide, N,N-dibutyl-n-octanamide, N,N-dibutyl-n-decanamide and N,N-dibutyl-n-dodecanamide, in particular N,N-dibutyl-n-octanamide, N,N-dibutyl-n-decanamide and N,N-dibutyl-n-dodecanamide.

The formula (I) above provides a general definition of the alkyl carboxylic acid amides. The compounds may be employed individually or in the form of a mixture. The amount of one or more compounds of the formula (I) for the use according to the invention in plant protection compositions can vary within a wide range, depending on the active substance. In a preferred embodiment, the acid amides of the formula (I) thus additionally act as solvents, while in another, likewise preferred embodiment, they act as additives for inhibiting the crystallization of triazole fungicides.

If the crystallization inhibitor, for example the acid amides of the formula (I), do not act as solvents, but as an exclusive additive for crystallization inhibition of active substances when spraying into plants, they are preferably present in the plant protection compositions according to the invention in an amount of from 1% to 30% by weight, especially preferably from 5% to 20%, in particular from 5% to 10%. If also acting as solvents, the crystallization inhibitor, for example the acid amides of the formula (I), may be present in amounts greater than 30% by weight, as required by the composition.

The suspoemulsion of the present invention may comprise one or more suitable dispersants in component (b). The suspoemulsion according to the invention preferably comprise a mixture of two different dispersants, most preferably those selected from the group consisting of the compounds mentioned under (b). Preferred dispersants are the substances mentioned below:

Methacrylic acid-methyl methacrylate-polyehyleneglycol graft copolymer, for example those commercially available under the name Atlox® 4913 (from Uniqema) and Tersperse 2500 (Huntsman Surfactant);

Tristyrylphenolethoxylates having an average of 16 to 60, preferably 16 to 50, oxyethylene units; moreover sulfated or phosphated tristylphenolethoxylates having an average of 6 to 20, preferably 7 to 16, oxyethylene units, and also salts of these substances; wherein specific mention may be made of commercial products known under the names Soprophor FLK (from Rhodia), Soprophor 3 D33 (from Rhodia), and Soprophor S/40-P (from Rhodia); and Propylene oxide/ethylene oxide block copolymers having at least 40 mol % polyoxyethylene units, a central polyoxypropylene portion preferably having a molecular mass of from 1500 to 2000. The products commercially available under the names Pluronic PE10100 (from BASF), Pluronic PE10500 (from BASF) and Pluronic 6800 (From BASF) may be mentioned by way of example.

Component (a) of the composition preferably comprises one or more polymeric stabilizers. Suitable polymeric stabilizers that may be used in the present invention include but are not limited to polypropylene, polyisobutylene, polyisoprene, copolymers of monoolefins and diolefins, polyacrylates, polystyrene, polyvinyl acetate, polyurethanes or polyamides. Suitable stabilizers are known in the art and commercially available.

The surfactants and polymeric stabilizers mentioned above are believed to impart the stability to the system.

In addition to the aforementioned components, the composition may comprise one or more further additives, as may be required. Additives for inclusion in the formulation are known in the art and commonly employed. Suitable additives which may be comprised in the suspoemulsion according to the invention are all customary formulation adjuvants such as organic solvents, anti-foaming agents, emulsifiers, anti-freezing agents, preservatives, antioxidants, colorants, thickeners and inert fillers.

Suitable anti-foaming agents include all substances which can normally be used for this purpose in agrochemical compositions. Particularly preferred anti-foaming agents are mixtures of polydimethylsiloxanes and perfluroalkylphosphonic acids, such as the silicone anti-foaming agents available, from GE or Compton.

Suitable organic solvents are not only alkanecarboxamides, such as those of the formula (I), but also all customary organic solvents which thoroughly dissolve the agrochemically active substances employed. The following may be mentioned as being preferred: N-methylpyrrolidone, N-octyl pyrrolidone, cyclohexyl-1pyrrolidone; or Solvesso 200, a mixture of paraffinic, isoparaffinic, cycloparaffinic and aromatic hydrocarbons. Suitable solvents are commercially available.

Suitable emulsifiers for inclusion in the compositions of the present invention are also known in the art and commercially available. Suitable emulsifiers include both ionic and non-ionic emulsifiers, such as fatty acid esters, fatty alcohol esters, ethers, alkyl sulphonates and aryl sulphonates. Other suitable surface active emulsifiers will also be known to the person skilled in the art.

Suitable preservatives include all substances which can normally be used for this purpose in agrochemical compositions of this type. Suitable examples which may be mentioned include Preventol® (from Bayer AG) and Proxel® (from Bayer AG).

Suitable antioxidants are all substances which can normally be used for this purpose in agrochemical compositions. Preference is given to butylated hydroxytoluene.

Suitable inert fillers include all substances which can normally be used for this purpose in agrochemical compositions and which do not act as thickeners. Preference is given to inorganic particles, such as carbonates, silicates and oxides, and also to organic substances, such as urea/formaldehyde condensates. By way of example, kaolin, rutile, silica, finely divided silica, silica gels, and natural and synthetic silicates, and also talc may be mentioned.

Suitable thickeners include all substances which can normally be used for this purpose in agrochemical compositions. For example xanthan gum, PVOH, cellulose, clay hydrated silicates, magnesium aluminum silicates or a mixture thereof. Again, such thickeners are known in the art and available commercially.

In addition, the suspoemulsion according to the invention also comprises water, present in the aqueous component (b).

The content of the individual components in the suspoemulsion according to the invention can be varied within a relatively wide range. Thus, the concentrations of the components as may be present are typically as follows:

of the active compounds from the group (i) of (b) are generally between 5% and 40% by weight, preferably between 8% and 25% by weight;

of the active compounds from the group (i) of (a) are generally between 5% and 30% by weight, preferably between 8% and 25% by weight;

of the crystal growth inhibitor from the group (ii) of (a) are generally between 5% and 30% by weight, preferably between 10% and 25% by weight;

of the polymeric stabilizer from the group (iii) of (a) are generally between 0.1% and 7.0%, and preferably from 0.2% to 4.0%;

of the dispersants from the group (ii) of (b) are generally between 3% and 10% by weight, preferably between 3% and 8% by weight;

of the water content in the suspoemulsion according to the invention from the group (iii) of (b) can be varied within a wide range. Depending on the other components, the water content is generally between 25% and 50% by weight;

of the one or more additives described above, the amount present is generally between 0% and 15% by weight, preferably between 0% and 13% by weight;

The suspoemulsions according to the present invention may be prepared using any suitable method. The preferred formulations are preferably prepared by the following procedure:

Step 1: Preparation of Triazole EC phase: The active triazole ingredient is mixed with the alkyl carboxylic acid amide and solvents at room temperature. The mixture may be allowed to stand for some time, for example about 30 minutes, before the addition of emulsifiers and the polymeric stabilizer under stirring until a homogeneous solution is achieved.

Step 2: Preparation of Dispersed particles of the Strobilurin active ingredient in a continuous water phase:

The Strobilurin active ingredient, along with suitable dispersants such as one or more tristyrylphenolethoxylates, a polymeric block copolymer and other optional additives such as anti-freezing agents anti-foaming agents, and the required amount of water are initially mixed well, preferably being finely milled using a horizontal agitating bead mill maintaining the process parameters like the average particle size d50 not to exceed 3 microns and for almost all the particles d90 not to exceed 6 microns.

Step 3: The oil phase produced in Step 1 is added to the water phase produced in Step 2 under continuous agitation for an optimum amount of time.

Step 4: Thickeners, such as polysaccharides or Xanthan gums, if to be included, are prepared in advance to enable them to be hydrated and be ready for the addition in the following step as mentioned as Step 5.

Step 5: Suitable quantity of the thickener, such as a gum, is added to the mixture produced in Step 4 and continuously agitated, preferably until the mixture is a homogeneous suspension.

The resulting suspension may be tested for the viscosity and pourability test and subsequently all the other physicochemical tests.

The suspoemulsions according to the invention are formulations which, even after prolonged storage at elevated temperatures or in the cold, remain stable as no crystal growth is observed. By the dilution with water, they can be converted into homogeneous spray fluids without finding the nozzles blocked as a result of crystallization of the active ingredients in the spray fluids. These spray fluids are suitable to be applied by customary methods, for example, by spraying, pouring or injecting.

The application rate of the suspoemulsion according to the invention can be varied within a relatively wide range, depending upon respective agrochemically active compounds and their content in the formulation.

With the aid of the suspoemulsion according to the invention, it is possible to apply agrochemically active compounds in a particularly advantageous manner to plants and/or their habitat. It has been found that the agrochemically active compounds comprised therein display better biological activity than that exhibited by the same active ingredients when incorporated in the corresponding conventional formulations.

In particular, as regards the protection of crop plants and materials, the application of the formulations according to the invention provides potent microbiocidal activity which can be employed for controlling unwanted microorganisms, such as fungi and bacteria. The formulations may be used for a wide range of crops, including, for example, transgenic, crops of useful plants and ornamentals, for example cereals such as wheat, barley, rye, oats, sorghum and millet, rice, cassava and maize, or else crops of peanut, sugar beet, cotton, soya, oilseed rape, tomato, pea and vegetables.

The suspoemulsions according to the invention are highly suitable for applying the agrochemically active compounds comprised therein to plants. No interfering side effects are observed upon dilution of the suspoemulsion according to the invention with water.

The invention is illustrated in greater detail by the following examples without being limited thereto.

PREPARATION EXAMPLES

Example 1

A suspoemulsion formulation was prepared as follows:

a) Emulsion Concentrate Preparation of Triazole EC Tebuconazole Phase:

The Active ingredient tebuconazole was mixed with N-methylpyrrolidone and N,N-diethyloctanamide at room temperature. It was allowed to stand for 30 minutes before the addition of the emulsifier Tween 80 and the polymeric stabilizer polystyrene under stirring until a homogeneous solution was achieved.

| Component | Composition (g) | Remark |
| --- | --- | --- |
| Tebuconazole Tech | 20 (as pure) | Active ingredient |
| N,N-diethyloctamide | 20 | Crystal growth inhibitor |
| N-methyl pyrrolidone | 5 | Solvent |
| Tween 80 | 3 | Emulsifier |
| polystyrene | 3 | Polymeric stabilizer | b) Preparation of Dispersed Particles of Strobilurin Active Ingredient Trifloxystrobin in a Continuous Water Phase:

| Component | Composition (g) | Remark |
| --- | --- | --- |
| Trifloxystrobin Tech | 10 (as pure) | Active ingredient |
| Atlox 4913 | 2.3 | dispersant |
| Soprophor FLK | 2.3 | dispersant |
| Propylene glycol | 4 | anti-freezing agent |
| 2% xanthan gum | 7.5 | thickener |
| Silicon oil | 0.5 | anti-foaming agent |
| water | 26.4 | carrier |

The Strobilurin active ingredient Trifloxystrobin, along with suitable dispersants Atlox 4913 and Soprophor FLK and other additives such as Antifreezing agent and Antifoaming agent and required amount of water were initially mixed well and finely milled using a horizontal agitating bead mill maintaining the process parameters, such as the average particle size d50 not to exceed 3 microns and for almost all the particles d90 not to exceed 6 microns.

c) Preparation of the Suspoemulsion

The oil phase (a) was added to water phase (b) under a continuous agitation for an optimum amount of time. Then suitable quantity of the thickener gum were added to the above mixture and continuously agitated until the mixture was a homogeneous suspension. The suspension was tested for the viscosity and pourability test and subsequently all the other necessary standard physico-chemical tests.

Example 2

A suspoemulsion formulation was prepared as follows:

a) Emulsion Concentrate Preparation of Triazole Cyproconazole EC Phase

| Component | Composition (g) | Remark |
|---|---|---|
| Cyproconazole Tech | 8 (as pure) | Active ingredient |
| N,N-diethyldecanamide | 15 | Penetration enhancer |
| Tween 80 | 3 | Emulsifier |
| polyvinyl acetate | 1 | Polymeric stabilizer |

The emulsion concentrate of Ciproconazole was prepared in the same general manner as set out in a) of Example 1 b) Preparation of Dispersed Particles of the Strobilurin Active Ingredient Azoxystrobin in a Continuous Water Phase:

| Component | Composition (g) | Remark |
|---|---|---|
| Azoxystrobin Tech | 20 (as pure) | Active ingredient |
| Tersperse 2500 | 4 | dispersant |
| Pluronic 6800 | 2 | dispersant |
| Propylene glycol | 4 | anti-freezing agent |
| 2% xanthan gum | 7.5 | thickener |
| Silicon oil | 0.5 | anti-foaming agent |
| water | 35 | carrier |

The preparation of the suspension concentrate of Azoxystrobin was carried out using the same general method as set out in b) of Example 1.

c) Suspoemulsion

The suspoemulsion was prepared using the same general procedure set out in c) of Example 1.

Example 3

A suspoemulsion formulation was prepared as follows:

a) Emulsion Concentrate Preparation of Triazole EC Phase

| Component | Composition (g) | Remark |
|---|---|---|
| tebuconazole Tech | 16 (as pure) | Active ingredient |
| N,N-diethyldodecanamide | 20 | Penetration enhancer |
| N,N-dimethylformamide | 5 | Solvent |
| Alkamuls OR/36 | 3 | Emulsifier |
| polyurethanes | 2 | Polymeric stabilizer |

The emulsion concentrate of Tebuconazole was prepared in the same general manner as set out in a) of Example 1.

b) Preparation of Dispersed Particles of the Strobilurin Active Ingredient Azoxystrobin in a Continuous Water Phase

| Component | Composition (g) | Remark |
|---|---|---|
| Azoxystrobin Tech | 8 (as pure) | Active ingredient |
| Soprophor 3 D33 | 2.3 | dispersant |
| Pluronic 10100 | 2.3 | dispersant |
| Propylene glycol | 4 | Antifreezing |
| 2% xanthan gum | 7.5 | thickener |
| Silicon oil | 0.5 | defoamer |
| water | 33.4 | carrier |

The preparation of the suspension concentrate of Azoxystrobin was carried out using the same general method as set out in b) of Example 1.

c) Suspoemulsion

The suspoemulsion was prepared using the same general procedure set out in c) of Example 1.

Example 4

A suspoemulsion formulation was prepared as follows:

a) Emulsion Concentrate Preparation of Prothioconazole EC Phase

| Component | Composition (g) | Remark |
|---|---|---|
| Prothioconazole Tech | 10 (as pure) | Active ingredient |
| N,N-dipropyloctamide | 10 | Penetration enhancer |
| N,N-dipropyldodecanamide | 10 | Penetration enhancer |
| N,N-dimethylformamide | 5 | Solvent |
| Alkamuls OR/36 | 3 | Emulsifier |
| polyurethanes | 2.5 | Polymeric stabilizer |

The emulsion concentrate of Prothioconazole was prepared in the same general manner as set out in a) of Example 1.

b) Preparation of Dispersed Particles of the Strobilurin Active Ingredient Fluoxastrobin in a Continuous Water Phase:

| Component | Composition (g) | Remark |
|---|---|---|
| Fluoxastrobin Tech | 10 (as pure) | Active ingredient |
| Tersperse 2500 | 2.5 | dispersant |
| Soprophor FLK | 1 | dispersant |
| Propylene glycol | 4 | Antifreezing |
| 2% xanthan gum | 7.5 | thickener |
| Silicon oil | 0.5 | defoamer |
| water | 38 | carrier |

The preparation of the suspension concentrate of Fluoxastrobin was carried out using the same general method as set out in b) of Example 1.

c) Suspoemulsion

The suspoemulsion was prepared using the same general procedure set out in c) of Example 1.

Example 5

A suspoemulsion formulation was prepared as follows:
a) Emulsion Concentrate Preparation of Tebuconazole EC Phase

| Component | Composition (g) | Remark |
|---|---|---|
| Tebuconazole Tech | 16 (as pure) | Active ingredient |
| N,N-dibutyldodecanamide | 20 | Penetration enhancer |
| N,N-dibutyloctanamide | 5 | Penetration enhancer |
| N,N-dimethylformamide | 5 | Solvent |
| Alkamuls OR/36 | 3 | Emulsifier |
| polyurethanes | 3 | Polymeric stabilizer |

The emulsion concentrate of Tebuconazole was prepared in the same general manner as set out in a) of Example 1.

b) Preparation of Dispersed Particles of the Strobilurin Active Ingredient Azoxystrobin in a Continuous Water Phase:

| Component | Composition (g) | Remark |
|---|---|---|
| Azoxystrobin Tech | 8 (as pure) | Active ingredient |
| Atlox 4913 | 2.3 | dispersant |
| Pluronic 6800 | 1.6 | dispersant |
| Propylene glycol | 4 | Antifreezing |
| 2% xanthan gum | 7.5 | thickener |
| Silicon oil | 0.5 | defoamer |
| water | 28.1 | carrier |

The preparation of the suspension concentrate of Azoxystrobin was carried out using the same general method as set out in b) of Example 1.

c) Suspoemulsion

The suspoemulsion was prepared using the same general procedure set out in c) of Example 1.

Field Evaluation 1

A composition prepared according to Example 1 was evaluated in the field in comparison with commercial formulations containing the same active ingredients.

| | Treatment Details | | |
|---|---|---|---|
| Number | Treatment Composition | Dosages (1/ha) | Dosages (g a.i./ha) |
| Control | Untreated Control | — | — |
| 1 | Folicur 250EC | 0.4 | 100 tebuc. |
| 2 | Nativo SC | 0.50 | 100 tebuc. + 50 Triflox. |
| 3 | Example 1 | 0.50 | 100 tebuc. + 50 Triflox. |

The above treatments were applied against soybean rust. Outdoors, soybeans were sprayed with the active compound preparations at an application rate such that the amounts of active compound stated in the above table were applied per hectare.

Folicur 250EC is a commercial formulation containing 25% tebuconazole. Nativo SC is a commercial formulation containing 20% tebuconazole+10% trifloxystrobin.

The second application was done at 14 days after the first application. The third application was done at 22 days after the second application. The first assessment was carried out at 14 days after the first application. The second assessment was carried out at 16 days after the second application. The third assessment was carried out at 19 days after the third application. Ten leaves were collected per plot, on 2 central lines, from the central area of the plants. The rust was assessed by determining the severity of rust of the plants and was expressed in percentage. The severity grade was determined according to the Diagrammatic Scale for Soybean Rust of EMBRAPA (Brazilian Agricultural Research Corporation).

Upon the first application, rust was already present in the area, with a Severity of 1.77%.

Results 1

| Treatments | Severity (%) of Rust/$1^{st}$ Assessment-14 DA1A | Severity (%) of Rust/2nd Assessment-16 DA2A | Severity (%) of Rust/3rd Assessment-28DA3A |
|---|---|---|---|
| Control | 8.98 | 55.35 | 94.33 |
| 1 | 0.45 | 1.31 | 15.65 |
| 2 | 1.28 | 3.94 | 33.40 |
| 3 | 0.48 | 0.38 | 6.56 |

Conclusions 1

Upon the $1^{st}$ Assessment, $2^{nd}$ Assessment, and $3^{rd}$ Assessment, it is noted that the treatments with the formulation of Example 1 are significantly better in controlling rust than Folicur alone, and much higher in their rust treatment than Nativo.

Field Evaluation 2

A composition according to Example 2 was evaluated in the field in comparison with commercial formulations containing the same active ingredients.

| | Treatment Details | | |
|---|---|---|---|
| Number | Treatment Composition | Dosages (1/ha) | Dosages (g a.i./ha) |
| 1 | Priori 250 SC | 0.24 | 60 Azoxy |
| 2 | Priori Xtra SC | 0.30 | 24 Cyproc. + 60 Azox. |
| 3 | Example 2 | 0.30 | 24 Cyproc. + 60 Azox. |

The above treatments were applied against soybean rust. Outdoors, soybeans were sprayed with the active compound preparations at an application rate such that the amounts of active compound stated in the above table were applied per hectare.

Priori is a commercial formulation containing 250 g/L azoxystrobin. Priori Xtra SC is a commercial formulation containing 80 g/L cyproconazole+200 g/L azoxystrobin.

The second application was done at 14 days after the first application. The third application was done at 22 days after the second application. The first assessment was carried out at 14 days after the first application. The second assessment was carried out at 16 days after the second application. The third assessment was carried out at 19 days after the third application. Ten leaves were collected per plot, on 2 central lines, from the central area of the plants. The rust was assessed by determining the severity of rust of the plants and was expressed in percentage. The severity grade was determined according to the Diagrammatic Scale for Soybean Rust of EMBRAPA (Brazilian Agricultural Research Corporation).

Upon the first application, Rust was already present in the area, with a Severity of 1.77%.

Results 2

| Treatments | Severity (%) of Rust/1st Assessment-14 DA1A | Severity (%) of Rust/2nd Assessment-16 DA2A | Severity (%) of Rust/3rd Assessment-28DA3A |
|---|---|---|---|
| 1 | 1.32 | 25.08 | 54.93 |
| 2 | 0.58 | 1.93 | 22.08 |
| 3 | 0.28 | 0.28 | 8.46 |

Conclusions 2

Upon the 1st Assessment, 2nd Assessment, and 3rd Assessment, it is noted that the treatments with the formulation of Example 1 gave significantly better results than Priori Xtra, and much higher efficacy than Priori.

Field Evaluation 3

A composition according to Example 3 was evaluated in the field in comparison with commercial formulations containing the same active ingredients.

Treatment Details

| Treatment Number | Treatment Composition | Dosages (1/ha) | Dosages (g a.i./ha) |
|---|---|---|---|
| 1 | Folicur 250EC | 0.32 | 80 tebuc. |
| 2 | Priori 250 SC | 0.16 | 40 azoxy. |
| 3 | Example 3 | 0.50 | 80 tebuc. + 40 azoxy |

The above treatments were applied against soybean rust. Outdoors, soybeans were sprayed with the active compound preparations at an application rate such that the amounts of active compound stated in the above table were applied per hectare.

Folicur 250EC is a commercial formulation containing 25% tebuconazole. Priori SC is a commercial formulation containing 25% azoxystrobin.

The second application was done at 14 days after the first application. The third application was done at 22 days after the second application. The first assessment was carried out at 14 days after the first application. The second assessment was carried out at 16 days after the second application. The third assessment was carried out at 19 days after the third application. Ten leaves were collected per plot, on 2 central lines, from the central area of the plants. The rust was assessed by determining the severity of rust of the plants and was expressed in percentage. The severity grade was determined according to the Diagrammatic Scale for Soybean Rust of EMBRAPA (Brazilian Agricultural Research Corporation).

Upon the first application, rust was already present in the area, with a Severity of 1.77%.

Results 3

| Treatments | Severity (%) of Rust/1st Assessment-14 DA1A | Severity (%) of Rust/2nd Assessment-16 DA2A | Severity (%) of Rust/3rd Assessment-28DA3A |
|---|---|---|---|
| 1 | 0.68 | 1.68 | 20.48 |
| 2 | 2.14 | 29.35 | 67.33 |
| 3 | 0.31 | 0.48 | 9.36 |

Conclusions 3

Upon the 1st Assessment, 2nd Assessment, and 3rd Assessment, it is noted that the treatments with the formulation of Example 1 are better in performance than Folicur alone, and much higher than Priori.

The invention claimed is:

1. An aqueous suspoemulsion, comprising:
   (a) a dispersed oil phase comprising:
      (i) at least one triazole active compound selected from the group consisting of tebuconazole, cyproconazole, and prothioconazole dissolved therein, wherein the triazole is present in a concentration between 5% and 30% by weight,
      (ii) at least one alkyl carboxylic acid amide selected from the group consisting of N,N-diethyl-n-octanamide, N,N-diethyl-n-decanamide, N,N-diethyl-n-dodecanamide, N,N-dipropyl-n-octanamide, N,N-dipropyl-n-dodecanamide, N,N-dibutyl-n-octanamide, and N,N-dibutyl-n-dodecanamide as a solvent and a crystal growth inhibitor; and
   (b) a continuous aqueous phase comprising:
      (i) at least one strobilurin active compound selected from the group consisting of trifloxystrobin, azoxystrobin, and fluoxastrobin, wherein the strobilurin is present in a concentration between 5% and 40% by weight;
      (ii) a dispersant selected from the group consisting of methacrylic acid-methyl methacrylate-polyethyleneglycol graft copolymers, tristyrylphenolethoxylates and/or propylene oxide/ethylene oxide block copolymer with 10% to 50% EO; and
      (iii) water.

2. The suspoemulsion as claimed in claim 1, wherein the active compound(s) of group (i) of (b) comprises one or more member selected from the group consisting of azoxystrobin, and trifloxystrobin.

3. The suspoemulsion as claimed in claim 1, wherein the active compound(s) of group (i) of (a) comprises one or more member selected from the group consisting of cyproconazole, and tebuconazole.

4. The suspoemulsion as claimed in claim 1, wherein the active compound of group (i) of (a) comprises tebuconazole and the active compound of group (i) of (b) comprises azoxystrobin.

5. The suspoemulsion as claimed in claim 1, wherein the active compound of group (i) of (a) comprises prothioconazole and the active compound of group (i) of (b) comprises fluoxastrobin.

6. The suspoemulsion as claimed in claim 1, wherein the active compound of group (i) of (a) comprises cyproconazole and the active compound of group (i) of (b) comprises azoxystrobin.

7. The suspoemulsion as claimed in claim 1, wherein the active compound of group (i) of (a) comprises tebuconazole and the active compound of group (i) of (b) comprises trifloxystrobin.

8. The suspoemulsion as claimed in claim 1, wherein said at least one alkyl carboxylic acid amide is selected from the group consisting of N,N-diethyl-n-octanamide, N,N-diethyl-n-decanamide, and N,N-diethyl-n-dodecanamide.

9. The suspoemulsion as claimed in claim 1, wherein said at least one alkyl carboxylic acid amide is selected from the group consisting of N,N-dipropyl-n-octanamide, and N,N-dipropyl-n-dodecanamide.

10. The suspoemulsion as claimed in claim 1, wherein said at least one alkyl carboxylic acid amide is selected from the group consisting of N,N-dibutyl-n-octanamide, and N,N-dibutyl-n-dodecanamide.

11. The suspoemulsion as claimed in claim 1, wherein component (a) further comprises:
   (iii) at least one polymeric stabilizer.

12. The suspoemulsion of claim 8, wherein the active compound of group (i) of (a) is tebuconazole, the active compound of group (i) of (b) is trifloxystrobin, and the carboxamide is N,N-diethyl-n-octanamide.

13. The suspoemulsion of claim 8, wherein the active compound of group (i) of (a) is cyproconazole, the active compound of group (i) of (b) is azoxystrobin, and the carboxamide is N,N-diethyl-n-decanamide.

14. The suspoemulsion of claim 8, wherein the active compound of group (i) of (a) is tebuconazole, the active compound of group (i) of (b) is azoxystrobin, and the carboxamide is N,N-diethyl-n-dodecanamide.

15. The suspoemulsion of claim 8, wherein the active compound of group (i) of (a) is prothioconazole, the active compound of group (i) of (b) is fluoxastrobin, and the carboxamide is N,N-dipropyl-n-octanamide and N,N-dipropyl-n-dodecanamide.

16. The suspoemulsion of claim 8, wherein the active compound of group (i) of (a) is tebuconazole, the active compound of group (i) of (b) is azoxystrobin, and the carboxamide is N,N-dibutyl-n-ocatanamide and N,N-dibutyl-n-dodecanamide.

17. The suspoemulsion as claimed in claim 1, wherein the at least one dispersant in (ii) of component (b) is selected from the group consisting of methacrylic acid-methyl methacrylate-polyethyleneglycol graft copolymers, tristyrylphenolethoxylates and/or propylene oxide/ethylene oxide block copolymer with 20% to 50% EO.

18. The suspoemulsion as claimed in claim 1, wherein the at least one dispersant in (ii) of component (b) is selected from the group consisting of methacrylic acid-methyl methacrylate-polyethyleneglycol graft copolymers, tristyrylphenolethoxylates and/or propylene oxide/ethylene oxide block copolymer with 30% to 40% EO.

19. The suspoemulsion as claimed in claim 1, wherein the dispersant includes 20% to 50% EO.

20. The suspoemulsion as claimed in claim 1, wherein the dispersant includes 30% to 40% EO.

* * * * *